(12) United States Patent
Olivares Martín et al.

(10) Patent No.: US 11,484,540 B2
(45) Date of Patent: Nov. 1, 2022

(54) METHOD FOR INCREASING EMBRYO IMPLANTATION RATE IN A FEMALE SUBJECT SUFFERING POLYCYSTIC OVARY SYNDROME

(71) Applicant: BIOSEARCH, S.A., Granada (ES)

(72) Inventors: Mónica Olivares Martín, Granada (ES); Juristo Fonollá Joyá, Granada (ES); María Paz Díaz-Ropero Medina, Granada (ES); José Luis López Larramendi, Madrid (ES); Nicolás Mendoza Ladrón De Guevara, Granada (ES)

(73) Assignee: Biosearch. S.A., Granada (ES)

( * ) Notice: Subject to any disclaimer, the term of this patent is extended or adjusted under 35 U.S.C. 154(b) by 7 days.

(21) Appl. No.: 16/766,062

(22) PCT Filed: Apr. 19, 2018

(86) PCT No.: PCT/EP2018/060077
§ 371 (c)(1),
(2) Date: May 21, 2020

(87) PCT Pub. No.: WO2019/101368
PCT Pub. Date: May 31, 2019

(65) Prior Publication Data
US 2020/0330495 A1  Oct. 22, 2020

(30) Foreign Application Priority Data
Nov. 23, 2017 (EP) .................................... 17382791

(51) Int. Cl.
*A61K 31/7004* (2006.01)
*A61P 15/00* (2006.01)
(Continued)

(52) U.S. Cl.
CPC ........ *A61K 31/7004* (2013.01); *A61K 9/0053* (2013.01); *A61K 9/4825* (2013.01); *A61P 15/00* (2018.01)

(58) Field of Classification Search
None
See application file for complete search history.

(56) References Cited

U.S. PATENT DOCUMENTS 9,259,410 B2   2/2016 Schutz

FOREIGN PATENT DOCUMENTS

| EP | 2502622 A1 | 9/2012 |
| EP | 2782559 A1 | 10/2014 |

(Continued)

OTHER PUBLICATIONS

Kolibianakis et al., "Effect of ovarian stimulation with recombinant follicle-stimulating hormone, gonadotropin releasing hormone antagonists, and human chorionic gonadotropin on endometrial maturation on the day of oocyte pick-up," Fertility and Sterility, vol. 78, Issue 5, 2002, pp. 1025-1029. (Year: 2002).*

(Continued)

*Primary Examiner* — Aradhana Sasan
(74) *Attorney, Agent, or Firm* — Sughrue Mion, PLLC

(57) ABSTRACT

The present invention relates to methods for increasing embryo implantation rate in a uterus, for preventing embryo implantation failure in a female subject suffering PCOS and for improving pregnancy rate comprising administering a composition comprising myo-inositol and D-chiro-Inositol in a weight ratio between 1:1 to 9:1 respectively to a female subject suffering PCOS. The invention also relates to a composition comprising myo-inositol and D-chiro-Inositol in a weight ratio between 1:1 to 9:1 respectively for use in the treatment or prevention of PCOS in a female subject, for use in the treatment or prevention of infertility in a female (Continued)

subject suffering polycystic ovary syndrome, or for use in preventing or reducing the risk of ovarian hyperstimulation syndrome in a female subject suffering polycystic ovary syndrome and subjected to ovary stimulation treatment. The invention also relates to a soft capsule comprising a) a soft capsule shell and b) a pharmaceutical composition comprising myo-inositol and D-chiro-Inositol in a weight ratio between 1:1 to 9:1 respectively.

16 Claims, 1 Drawing Sheet

(51) Int. Cl.
A61K 9/00 (2006.01)
A61K 9/48 (2006.01)

(56) References Cited

FOREIGN PATENT DOCUMENTS

| EP | 2875809 | A1 | 5/2015 |
|---|---|---|---|
| EP | 3178474 | A1 | 6/2017 |
| JP | 2006213684 | A | 8/2006 |
| WO | 201212693 | A2 | 1/2012 |
| WO | 2013076121 | A1 | 5/2013 |
| WO | 2017179012 | A1 | 10/2017 |

OTHER PUBLICATIONS

Baillargeon et al., "Altered D-Chiro-Inositol Urinary Clearance in Women with Polycystic Ovary Syndrome", Diabetes Care, Feb. 2006, pp. 300-305, vol. 29, No. 2.
Benelli et al., "A Combined Therapy with Myo-Inositol and D-Chiro-Inositol Improves Endocrine Parameters and Insulin Resistance in PCOS Young Overweight Women", International Journal of Endocrinology, 2016, pp. 1-5, vol. 2016, Hindawi Publishing Corporation.
Bevilacqua et al., "Results from the International Consensus Conference on Myo-Inositol and D-Chiro-Inositol in Obstetrics and Gynecology—Assisted Reproduction Technology", Gynecological Endocrinology, 2015, pp. 1-6, vol. 31, No. 6.
Bizzarri et al., "Inositol: History of an Effective Therapy for Polycystic Ovary Syndrome", European Review for Medical and Pharmacological Services, 2014, pp. 1896-1903, vol. 18.
Bode et al., "Hirsutism in Women", American Family Physician, Feb. 2012, pp. 373-380, vol. 85, No. 4.
Bozdag et al., "The Prevalence and Phenotypic Features of Polycystic Ovary Syndrome: A Systematic Review and Meta-analysis", Human Reproductive, Sep. 2016, pp. 2841-2855, vol. 31, No. 12, Oxford University Press.
Brusco et al., "Inositol: Effects on Oocyte Quality in Patients Undergoing ICSI—An Open Study", European Review for Medical and Pharmacological Sciences, 2013, pp. 3095-3102, Vo. 17, No. 22.
Calaf et al., "Long-term Efficacy and Tolerability of Flutamide Combined with Oral Contraception in Moderate to Severe Hirsutism: A 12-Month, Double-Blind, Parallel Clinical Trial", The Journal of Clinical Endocrinology & Metabolism, Sep. 2007, pp. 3446-3452, vol. 92, No. 9.
Carlomagno et al., "Myo-Inositol in a New Pharmaceutical Form: A Step Forward to a Broader Clinical Use", Expert Opin. Drug Deliv., 2012, pp. 267-271, vol. 9, No. 3.
Carlomagno et al., "The D-chiro-inositol Paradox in the Ovary", Fertility and Sterility, Jun. 2011, pp. 2515-2516, vol. 95, No. 8, Elsevier Inc.
Cheang et al., "A Paradox: The Roles of Inositolphosphoglycans in Mediating Insulin Sensitivity and Hyperandrogenism in the Polycystic Ovary Syndrome", Hormones, 2004, pp. 244-251, vol. 3, No. 4.

Ciotta et al., "Effects of Myo-Inositol Supplementation on Oocyte's Quality in PCOS Patients: A Double Blind Trial", European Review for Medical and Pharmacological Sciences, 2011, pp. 509-514, vol. 15, No. 5.
Colazingari et al., "The Combined Therapy Myo-Inositol Plus D-Chiro-Inositol, rather than D-Chiro-Inositol, is able to Improve IVF Outcomes: Results from a Randomized Controlled Trial", Arch Gynecol Obstet, 2013, pp. 1405-1411, vol. 288, No. 6.
De Leo et al., "Evaluation of the Treatment with D-Chiro-Inositol on Levels of Oxidative Stress in PCOS Patients", Minerva Ginecologica, 2012, pp. 531-538, vol. 64, No. 6.
De Leo et al., "Evaluation of the Treatment with D-Chiro-Inositol on Levels of Oxidative Stress in PCOS Patients", Minerva Ginecologica, 2012, pp. 531-538, vol. 64, No. 6 [Abstract].
De Leo et al., "Oxidative Stress in Folicular Fluid from Women with Polycystic Ovary Syndrome and the Effect of Inositiol", European Society of Human Reproduction and Embryology, 2013.
Formuso et al., "Myo-Inositol vs. D-Chiro-Inositol in PCOS Treatment", Minerva Ginecologica, 2015, pp. 321-325, vol. 67, No. 4.
Galletta et al., "Bye-bye Chiro-Inositol—Myo-Inositol: True Progress in the Treatment of Polycystic Ovary Syndrome and Ovulation Induction", European Review for Medical and Pharmacological Sciences, 2011, pp. 1212-1214, vol. 15, No. 10.
Genazzani et al., "Modulatory Role of D-Chiro-Inositol (DCI) on LH and Insulin Secretion in Obese PCOS Patients", Gynecological Endocrinology, 2014, pp. 438-443, vol. 30, No. 6.
Genazzani et al., "Myo-Inositol Modulates Insulin and Luteinizing Hormone Secretion in Normal Weight Patients with Polycystic Ovary Syndrome", The Journal of Obstetrics and Gynaecology Research, 2014, pp. 1353-1360, vol. 40, No. 5, The Authors.
Heimark et al., "Decreased Myo-Inositol to Chiro-Inositol (M/C) Ratios and Increased M/C Epimerase Activity in PCOS Theca Cells Demonstrate Increased Insulin Sensitivity Compared to Controls", Endocrine Journal, 2014, pp. 111-117, vol. 61, No. 2.
International Preliminary Report on Patentability for PCT/EP2018/060077 dated May 26, 2020.
International Search Report with Written Opinion for PCT/EP2018/060077 dated May 30, 2018.
Isabella et al., "Does Ovary Need D-Chiro-Inositol?", Journal of Ovarian Research, 2012, p. 1-5, vol. 5, No. 14.
Iuorno et al., "Effects of D-Chiro-Inositol in Lean Women with the Polycystic Ovary Syndrome", Endocriine Practice, 2002, pp. 417-423, vol. 8, No. 6.
La Marca et al., "The Menstrual Cycle Regularization Following D-Chiro-Inositol Treatment in PCOS Women: A Retrospective Study", Gynecological Endocrinology, 2015, pp. 52-56, vol. 31, No. 1.
Lagana et al., "Know Your Enemy: The Rationale of Using Inositol in the Treatment of Polycystic Ovary Syndrome, Endocrinology & Metabolic Syndrome", 2013, pp. 1-2, vol. 2, Issue 3.
Malvasi et al., "Myo-Inositol, D-Chiro-Inositol, Folic Acid and Manganese in Second Trimester of Pregnancy: A Preliminary Investigation", European Review for Medical and Pharmacological Sciences, 2014, pp. 270-274, vol. 18, No. 2.
Minozzi et al., "The Combined Therapy Myo-Inositol Plus D-Chiro-Inositol, in a Physiological Ratio, Reduces the Cardiovascular Risk by Improving the Lipid Profile in PCOS Patients", European Review for Medical and Pharmacological Sciences, 2013 pp. 537-540, vol. 17, No. 4.
Nestler et al., "Ovulatory and Metabolic Effects of D-Chiro-Inositol in the Polycystic Ovary Syndrome", The New England Journal of Medicine, 1999, pp. 1314-1320, vol. 340, No. 17, Massachusetts Medical Society.
Niwa et al., "Gas Chromatographic-Mass Spectrometric Analysis of Polyols in Urine and Serum of Uremic Patients. Identification of New Deoxyalditols and Inositol Isomers", Journal of Chromatography, 1983, pp. 25-39, vol. 277, Elsevier Science Publishers B.V.
Nordio et al., "The Combined Therapy with Myo-Inositol and D-Chiro-Inositol Reduces the Risk of Metabolic Disease in PCOS Overweight Patients Compared to Myo-Inositol Supplementation Alone", European Review for Medical and Pharmacological Sciences, 2012, pp. 575-581, vol. 16, No. 5.

(56) References Cited

OTHER PUBLICATIONS

Papaleo et al., "Myo-Inositol May Improve Oocyte Quality in Intracytoplasmic Sperm Injection Cycles. A Prospective, Controlled, Randomized Trial", Fertility and Sterility, 2009, pp. 1750-1754, vol. 91, No. 5, American Society for Reproductive Medicine.

Piomboni et al., "Protein Modification as Oxidative Stress Marker in Follicular Fluid from Women with Polycystic Ovary Syndrome: The Effect of Inositol and Metformin", J Assist Reprod Genet, 2014, pp. 1269-1276, vol. 31, No. 10.

Pizzo et al., "Comparison between Effects of Myo-Inositol and D-Chiro-Inositol on Ovarian Function and Metabolic Factors in Women with PCOS", Gynecological Endocrinology, 2014, pp. 205-208, vol. 30, No. 3.

Rotterdam, "Revised 2003 Consensus on Diagnostic Criteria and Long-Term Health Risks Related to Polycystic Ovary Syndrome (PCOS)", Human Reproduction, 2004, pp. 41-47, vol. 19, No. 1, European Society of Human Reproduction and Embryology.

Rotterdam, "Revised 2003 Consensus on Diagnostic Criteria and Long-Term Health Risks Related to Polycystic Ovary Syndrome", Fertility and Sterility, 2004, pp. 19-25, vol. 81, No. 1, American Society for Reproductive Medicine.

Salley et al., "Glucose Intolerance in Polycystic Ovary Syndrome—A Position Statement of the Androgen Excess Society", The Journal of Clinical Endocrinology Metabolism, 2007, pp. 4546-4556, vol. 92, No. 12, The Endocrine Society.

Third Party Observation for PCT/EP2018/060077 filed on Mar. 20, 2020.

Third Party Observation for PCT/EP2018/060077 filed on Mar. 23, 2020.

U.S. National Library of Medicine, "Evaluation of the Mixture Myoinositol:D-Chiro-Inositol 3.6:1 in Women with Polycystic Ovary Syndrome", Clinical Trials, 2017, pp. 1-7.

Unfer et al., "Hyperinsulinemia Alters Myoinositol to D-Chiroinositol Ratio in the Follicular Fluid of Patients with PCOS", Reproductive Sciences, 2014, pp. 854-858, vol. 21, No. 7.

Unfer et al., "Myo-Inositol rather than D-Chiro-Inositol is able to Improve Oocyte Quality in Intracytoplasmic Sperm Injection Cycles: A Prospective, Controlled, Randomized Trial", European Review for Medical and Pharmacological Sciences, 2011, pp. 452-457, vol. 15, No. 4.

Unfer et al., "Updates on the Myo-Inositol Plus D-Chiro-Inositol Combined Therapy in Polycystic Ovary Syndrome", Expert Review of Clinical Pharmacology, 2014, pp. 623-631, vol. 7, No. 5.

Yildiz et al., "Visually Scoring Hirsutism", Human Reproduction Update, 2010, pp. 51-64, vol. 16, No. 1.

Sundyota Numandis, ReDiva | ReDiva Ma Product Monograph, 2015, pp. 1-39.

\* cited by examiner

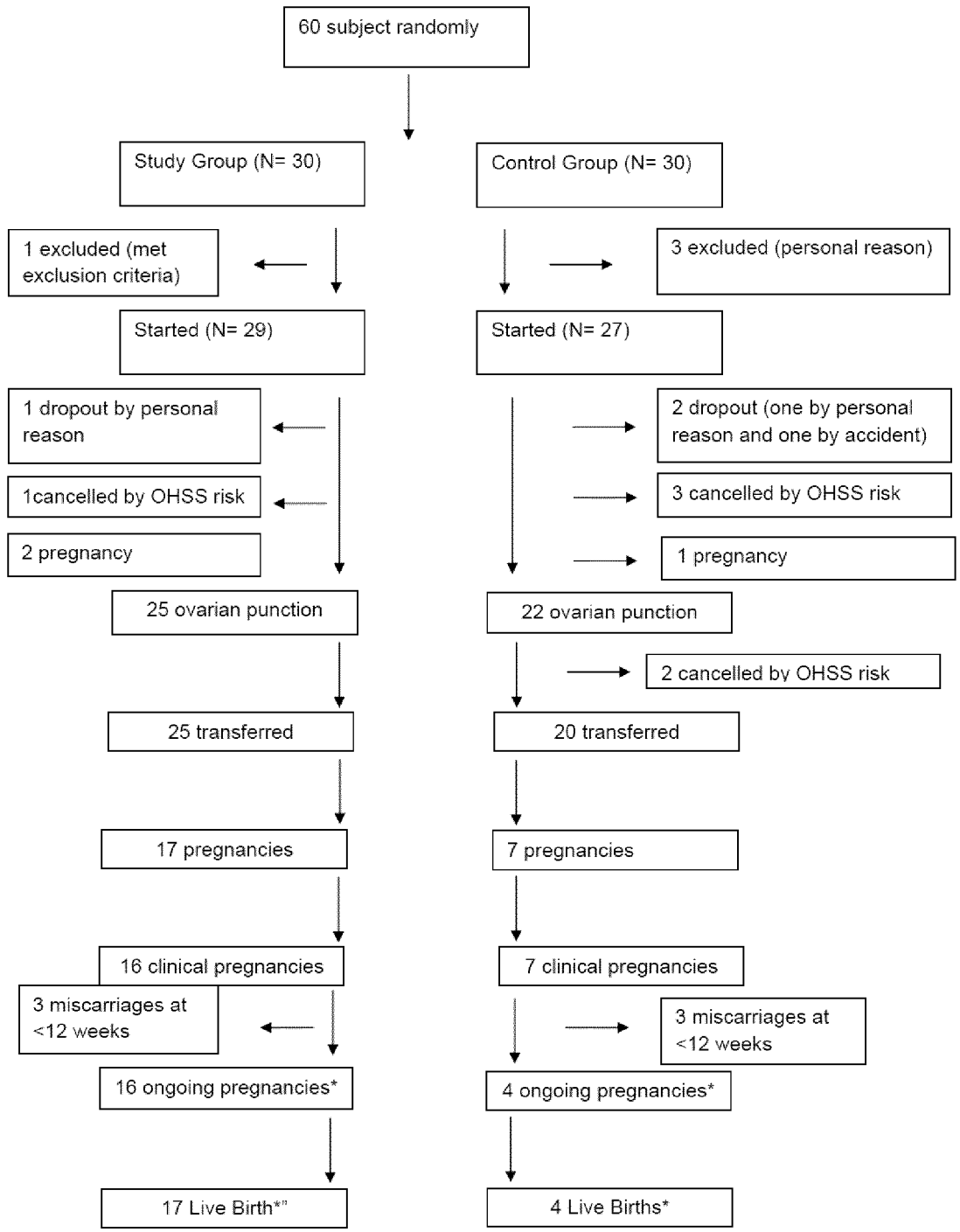

METHOD FOR INCREASING EMBRYO IMPLANTATION RATE IN A FEMALE SUBJECT SUFFERING POLYCYSTIC OVARY SYNDROME

CROSS-REFERENCE TO RELATED APPLICATIONS

This patent application is a National Phase Application under 35 U.S.C. § 371 U.S. of International Patent Application No. PCT/EP2018/060077, filed Apr. 19, 2018, which claims priority to European Patent Application No. 17382791.6, filed Nov. 23, 2017, each of which is incorporated by reference herein in its entirety.

FIELD OF THE INVENTION

The present invention relates to the field of methods for increasing embryo implantation as well as of treatment of symptoms of polycystic ovary syndrome (PCOS).

BACKGROUND OF THE INVENTION

Polycystic ovary syndrome (PCOS) is a complex and heterogeneous disease in which gynecological disorders with metabolic problems coexist. The diagnosis of the PCOS has been reached by consensus in Rotterdam of the European Society of Human Reproduction and Embryology and the American Society for Reproductive Medicine, requiring two out of the three criteria: clinical and/or biochemical hyperandrogenism, oligo- or anovulation and ultrasound polycystic ovaries (Rotterdam ESHRE/ASRM-Sponsored PCOS Consensus Workshop Group 2004). However, use of the Rotterdam criteria will probably increase the high prevalence of PCOS, and currently, PCOS is the most common endocrinopathy in women, affecting 7-14% of women of childbearing age worldwide (Bozdag et al., Hum Reprod. 2016 December; 31(12):2841-2855).

The manifestations of hyperandrogenism (acne, seborrhoea, hirsutism and androgenic alopecia) and obesity, usually of the android type, are clinical manifestations of PCOS as well as oligomenorrhea, secondary amenorrhea and dysfunctional metrorrhagia due to endometrial hyperplasia. It is also characteristic of women with PCOS to increase parameters related to cardiovascular risk, deregulation of ovarian hormones (responsible for the appearance of cysts) and increased insulin resistance.

The treatment is aimed at correcting hyperandrogenism, chronic anovulation and metabolic alterations associated with insulin resistance and hyperinsulinism. In this regard, compounds such as metphormin, troglitazone and inositols (D-chiro-inositol (DCI) or Myo-inositol (MI)) have been used in order to improve insulin resistance.

In the case of MI, although it has also been effective in the treatment of PCOS, the doses required are up to 4 times higher than those used with DCI. MI is the most abundant inositol in the body and is a precursor of DCI which is synthesized from MI by an insulin-dependent epimerase. Conversion levels are specific to each organ making the MI/DCI ratio vary from one organ to another.

At the reproductive level, inositol has been detected in the ovarian follicle and also appears to intervene in oocyte meiosis. In the ovary of women with PCOS, unlike in all other tissues, there is an MI deficiency accompanied by an increase in the proportion of DCI. It has been observed that there is an association of dietary supplementation with MI with ovulation and spontaneous pregnancies. Indeed, in randomized clinical trials, reproductive variables such as FSH requirements, number of mature oocytes and embryo quality in PCOS patients undergoing fertility treatments have been improved after MI treatment, as well as improvements in the lipid profile and in the overweight (Papaleo E. et al., Fertik Steru 2009; 91:1750-4; Ciotta K. et al., Eur Rev Med Pharma Col Sci 2011; 15509-14). MI supplementation has been shown to be more effective in in vitro fertilization than DCI supplementation (De Leo V. et al., Minerva Ginecol 2012; 64 (6):531-8). This is coherent with the key role of MI in quality of oocytes. In fact it has been reported that DCI, at high concentration, might negatively affect to oocitary quality (Isabelle et al, Journal of Ovarian Research 2012, 5:14).

The studies performed with combination MI/DCI for fertility problems associated to PCOS were performed with the ratio 40:1. Authors recommend the use of this ratio based in the plasmatic ratio of the stereoisomers (Unfer V. et al., Expert Rev Clin Pharmacol. 2014; 7(5):623-31). The proportion of DCI is recommended to be low because ovary in PCOS is deficient in MI and has over production of DCI due to a dysregulation of the epimerase activity. Moreover, a previous study observed a negative effect of increasing doses on quality oocytes (Isabella R. et al., J Ovarian Res. 2012 May 15; 5(1):14). This study showed that administration of DCI to women suffering PCOS increase the immature oocytes, reduced the number of mature MII oocytes and the number of grade I embryos.

Therefore, there is still a need in the art to provide alternative and effective treatments of fertility problems and methods for increasing embryo implantation rate in female subjects suffering PCOS.

SUMMARY OF THE INVENTION

The inventors has surprisingly found that the administration to women suffering PCOS of a combination of MI/DCI in a weight ratio between 1:1 to 9:1 significantly improves the rate of pregnancy due improvement in the embryo implantation phase despite the high proportion of DCI with respect to MI. In addition, another relevant finding is that women suffering PCOS and undergoing assisted reproductive technology show lower risk of suffering ovarian hyperstimulation when treated with a combination of MI/DCI in a weight ratio between 1:1 to 9:1.

Therefore, in a first aspect the invention relates to a method for increasing embryo implantation rate in a uterus comprising administering a composition comprising myo-inositol and D-chiro-Inositol in a weight ratio between 1:1 to 9:1 respectively to a female subject suffering polycystic ovary syndrome.

The invention also relates to a method for preventing embryo implantation failure in a female subject suffering polycystic ovary syndrome comprising administering a composition comprising myo-inositol and D-chiro-lnositol in a weight ratio between 1:1 to 9:1 to said female.

In another aspect, the invention relates to a method for improving pregnancy rate comprising administering a composition comprising myo-inositol and D-chiro-Inositol in a weight ratio between 1:1 to 9:1, respectively, to a female subject suffering polycystic ovary syndrome. In another aspect, the invention relates to a method for promoting pregnancy in female subject suffering polycystic ovary syndrome comprising administering to said female subject a composition comprising myo-inositol and D-chiro-Inositol in a weight ratio between 1:1 to 9:1, respectively.

In another aspect, the invention relates to a composition comprising myo-inositol and D-chiro-lnositol in a weight ratio between 1:1 to 9:1 respectively for use in the treatment or prevention of polycystic ovary syndrome in a female subject.

In a another aspect, the invention relates to a composition comprising myo-inositol and D-chiro-lnositol in a weight ratio between 1:1 to 9:1, respectively, for use in the treatment or prevention of infertility in a female subject suffering polycystic ovary syndrome.

In another aspect, the invention relates to a composition comprising myo-inositol and D-chiro-lnositol in a weight ratio between 1:1 to 9:1, respectively, for use in preventing or reducing the risk of ovarian hyperstimulation syndrome in a female subject suffering polycystic ovary syndrome and subjected to ovary stimulation treatment.

In another aspect, the invention relates to a soft capsule comprising:
a) a soft capsule shell and
b) a pharmaceutical composition comprising myo-inositol and D-chiro-lnositol in a weight ratio between 1:1 to 9:1 respectively.

BRIEF DESCRIPTION OF THE DRAWINGS

FIG. 1. Flow chart of the study.

DETAILED DESCRIPTION OF THE INVENTION

Methods

In one aspect, the invention relates to a method for increasing embryo implantation rate in a uterus comprising administering a composition comprising myo-inositol and D-chiro-Inositol in a weight ratio between 1:1 and 9:1 respectively to a female subject suffering polycystic ovary syndrome.

The invention also relates to a method for preventing embryo implantation failure in a female subject suffering polycystic ovary syndrome comprising administering a composition comprising myo-inositol and D-chiro-lnositol in a weight ratio between 1:1 to 9:1 to said female.

Prevention refers to reduced susceptibility to a clinical condition, particularly embryo implantation failure.

Reference herein to "embryo" is intended to include a blastula, blastocyst, fertilized ovum or an organism in its early stages of development, especially before it has reached a distinctively recognizable form that is to be implanted into a female recipient.

The term "implantation" is used to describe the process of attachment and invasion of the uterus endometrium by the blastocyst (conceptus) in placental animals.

"Implantation rate" is the percentage of embryos which successfully undergo implantation compared to the number of embryos transferred in a given period. In practice, it is generally calculated as the number of intrauterine gestational sacs observed by transvaginal ultrasonography divided by the number of transferred embryos. As a way of illustrative sample it has been reported an implantation rate in in vitro fertilization (IVF) of 37% at a maternal age of less than 35 years, 30% at 35 to 37 years, 22% at 38 to 40 years, and 12% at 41 to 42 years.

"Increased implantation rate", as used in the present invention relates to higher percentage of embryos which successfully undergo implantation in a treated subject according to the invention compared to the percentage of embryos which successfully undergo implantation in an untreated subject. In a preferred embodiment, the implantation rate is increased by at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180% or more.

The implantation according to the invention may be a natural implantation or implantation subsequent to an assisted reproductive technology such as artificial insemination or assisted reproductive technology (ART), in vitro fertilization (IVF), Intracytoplasmic sperm injection (ICSI), or following transplantation of a fresh or frozen or otherwise preserved embryo(s) and gametes, gamete intrafallopian transfer (GIFT) or zygote intrafallopian transfer (ZIPT). In a preferred embodiment, the implantation is due to in vitro fertilization (IVF). In a preferred embodiment the assisted reproductive technology is ICSI.

"Implantation failure", as used herein is considered when embryos of good quality fail to implant following natural conception or several in vitro fertilization (IVF) treatment cycles. Considering the current success rate of IVF treatments and the mean number of embryos transferred in each cycle, implantation failure is usually defined as failure of implantation in at least three consecutive IVF attempts, in which 1-2 embryos of high grade quality are transferred in each cycle.

"In vitro fertilization", IVF, as used herein relates to a process of fertilisation where and egg is combined with sperm outside the body, in vitro. The IVF procedure is performed in a known manner. Details about the removal of the oocytes from follicles in the ovary, culturing of the isolated oocytes, the culture medium to be used, the fertilisation with sperm and the transfer of the embryo to the fallopian tube can be found in the literature, e.g. in U.S. Pat. No. 5,693,534.

As a consequence of the method of the invention, the pregnancy rate is improved. Therefore the invention also relates to a method for improving pregnancy rate comprising administering a composition comprising myo-inositol and D-chiro-Inositol in a weight ratio between 1:1 to 9:1, respectively, to a female subject suffering polycystic ovary syndrome. All the preferred embodiments of the method for increasing embryo implantation are also applied to the method for preventing embryo implantation failure and to a method for improving pregnancy rate.

In a preferred embodiment of the method for improving pregnancy rate, the composition comprising myo-inositol and D-chiro-lnositol in a weight ratio between 1:1 to 9:1, respectively, does not comprises folic acid.

"Improved pregnancy rate" is intended to include a positive pregnancy outcome or improved perinatal survival or general viability following artificial insemination with processed semen or natural insemination or following transplantation of fresh or frozen or otherwise preserved embryos. The pregnancy rate may be defined in various ways, in an illustrative non limitative example may be based on fetal heart motion observed in ultrasound examination. In a preferred embodiment, the pregnancy rate is increased by by at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180% or more. In a more preferred embodiment, the method of the invention relates to a method for improving pregnancy rate to at least 50%.

In another preferred embodiment, the method of the invention is directed to a method for improving pregnancy rate as a consequence of IVF.

According to the method of the invention, the composition is to be administered to a female subject suffering polycystic ovary syndrome.

The term "female subject" refers to a female mammal and include, but are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of preferred embodiments are humans.

"Polycystic ovary syndrome", as used herein relates to a common health problem caused by an imbalance of reproductive hormones. Signs and symptoms of PCOS include irregular or no menstrual periods, heavy periods, excess body and facial hair, acne, pelvic pain, difficulty getting pregnant, and patches of thick, darker, velvety skin. Associated conditions include type 2 diabetes, obesity, obstructive sleep apnea, heart disease, mood disorders, and endometrial cancer.

In a preferred embodiment, the female subject is in a reproductive age, between menarche and menopause. In another preferred embodiment, the female subject is treated for ovarian stimulation and oocyte production. In another preferred embodiment, the female subject is a human female subject. In another preferred embodiment, the human female subject shows a BMI below 30 kg/m$^2$, therefore, the female subject does not show obesity. In another preferred embodiment, the female subject is treated with folic acid.

In another preferred embodiment, the female subject is subjected to an ovarian stimulation treatment after the administration of the composition according to the method of the invention.

"Ovary stimulation treatment", as used herein relates to the use of drugs to stimulate the growth of one or more follicles. Different drugs can be used, such as Clomiphene Citrate, Gonadotropins (FSH and LH) or Human Chorionic Gonadotropins (hCG). In a preferred embodiment, the ovary stimulation treatment is gonadotropin-releasing hormone antagonist and FSH.

The composition used in the method of the invention comprises myo-inositol and D-chiro-lnositol in a weight ratio between 1:1 to 9:1, respectively. The present invention encompasses all the possible ratios within the range 1:1 to 9:1.

"Composition", as used in the present invention, relates to any composition of matter comprising the components of the invention, i.e., myo-inositol and D-chiro-inositol. It will be understood that the composition may be formulated as a single component or, alternatively, it can be provided as separated formulations which may then combined for their joint administration. The compositions of the invention may also be provided as a kit-of-parts wherein each of the components is separately formulated but packaged in a single container. The term composition, according to the invention, includes all types of solid, semisolid and fluid compositions. The term composition also includes a nutritional composition and a nutraceutical.

The term "nutritional composition" of the present invention refers to the food that, regardless of providing nutrients to the subject that takes it, produces a beneficial effect to one or more functions of the organism, providing better health and wellness. Accordingly, such a nutritional composition may be used for the prevention and/or treatment of a disease or a disease causing factor or in a method of the invention. Therefore, the term "nutritional composition" of the present invention can be used as a synonym for functional food or food for specific medical food or nutritional purposes. A nutritional composition has similar appearance that a conventional food and is consumed as part of a normal diet.

By "nutraceutical", a word derived from nutrition and pharmaceutical, means a product made from a food, but can be found in pill form, powders and other dosage forms not usually associated with food and having beneficial properties for the treatment and/or prevention of diseases.

"Myo-inositol", MI, former names meso-inositol or i-inositol, or cis-1,2,3,5-trans-4,6-cyclohexanehexol as used herein relates to the most widely steroisomer form of inositol in nature.

"D-chiro-inositol", DCI, 1D-chiro-Inositol as used herein relates to cis-1,2,4-trans-3,5,6-cyclohexanehexol 1D-1,2,4/3,5,6-cyclohexanehexol, a component of an inositol phosphoglycan which enhances the way insulin works in the body.

In a preferred embodiment, the composition to be administered according to the method for increasing embryo implantation rate comprises myo-inositol: D-chiroinositol in a weight ratio range between 1:1 to 3:1, more preferably 1:1, 1.5:1, 2:1, 2.5:1 or 3:1. In another referred embodiment, the myo-inositol: D-chiroinositol is in a weight ratio range between 3:1 to 5:1, more preferably 3:1, 3.5:1, 4:1, 4.5:1 or 5:1. In another referred embodiment, the myo-inositol: D-chiroinositol is in a weight ratio range between 5:1 to 7:1, more preferably 5:1, 5.5:1, 6:1, 6.5:1 or 7:1. In another referred embodiment, the myo-inositol: D-chiroinositol is in a weight ratio range between 7:1 and 9:1, more preferably 7:1, 7.5:1, 8:1, 8.5:1 or 9:1.

In another preferred embodiment, the myo-inositol: D-chiroinositol is in a weight ratio range between 2:1 to 5:1, more preferably between 2:1, 2.5:1, 3:1, 3.5:1, 4:1, 4.5:1 and 5:1. In another preferred embodiment, the weight ratio of myo-inositol:D-chiroinositol is 3.1:1, 3.2:1, 3.3:1, 3.4:1, 3.5:1, 3.6:1, 3.7:1, 3.8:1 or 3.9:1. In a more preferred embodiment, the weight ratio of myo-inositol:D-chiroinositol is 3.66:1.

In another preferred embodiment, the composition to be administered according to the methods of the invention consists of myo-inositol and D-chiro-lnositol in a weight ratio between 1:1 to 9:1, respectively as the active principles.

"Active principle or active ingredient", as used herein relates to drugs or chemicals in a pharmaceutical preparation that exert an effect pharmacologically, not including the pharmaceutical excipient or carrier.

As the person skilled in the art can understand the desirable weight ratio of myo-inositol:D-chiroinositol can be obtained with different amounts of myo-inositol and D-chiroinositol, all of them encompasses in the present invention. In a preferred embodiment of the method of the invention the contents of myo-inositol and D-chiro-Inositol in the composition are 550 mg of myo-inositol and 150 mg of D-chiro-lnositol or 1100 mg of myo-inositol and 300 mg of D-chiro-Inositol. In another preferred embodiment, the contents of myo-inositol is between 1000-2000 mg and the contents of D-chiro-inositol is between 300-500 mg.

In another preferred embodiment, the composition to be administered according to the methods of the invention comprises between 1000 mg and 2000 mg of myo-inositol. In another preferred embodiment, the composition to be administered according to the methods of the invention comprises between 300 mg and 500 mg of D-chiro-lnositol. In another preferred embodiment, the contents of myo-inositol and D-chiro-Inositol in the composition are 1000 mg of myo-inositol and 150 mg of D-chiro-Inositol. In another preferred embodiment, the contents of myo-inositol and D-chiro-Inositol in the composition are 2000 mg of myo-inositol and 300 mg of D-chiro-lnositol.

The composition to be administered in the method according to the invention can be in the form of a pharmaceutical composition comprising myo-inositol: D-chiroinositol in a weight ratio range between 1:1 to 9:1, respectively formulated with pharmaceutically acceptable excipients and/or carriers to obtain a pharmaceutical composition.

"Pharmaceutical composition" as used herein, relates to compositions and molecular entities that are physiologically tolerable and do not typically produce an allergic reaction or a similar unfavorable reaction as gastric disorders, dizziness and suchlike, when administered to a human or animal.

The term "excipient or carrier" refers to a vehicle, diluent or adjuvant that is administered with the active ingredient. Preferably, the term "pharmaceutically acceptable" means it is approved by a regulatory agency of a state or federal government and/or is included in the U.S. Pharmacopoeia and/or other generally recognized pharmacopoeia for use in animals, and more particularly in humans.

Suitable pharmaceutically acceptable excipients include, for example, water, salt solutions, alcohol, oils including those of petroleum, animal, vegetable or synthetic origin, such as peanut oil, soybean oil, mineral oil, sunflower oil, sesame oil and similar; polyethylene glycols, gelatin, lactose, amylose, magnesium stearate, talc, surfactants, silicic acid, viscous paraffin, glycerine, perfume oil, monoglycerides and diglycerides of fatty acids, fatty acid esters petroetrals, hydroxymethyl cellulose, polyvinylpyrrolidone and similar; softisan, waxes, such as yellow wax of bees clover, lecithins such as sunflower lecithin.

The nutritive compositions or nutraceuticals used in the method of the invention may be formulated with the usual excipients and adjuvants for oral compositions or food supplements, such as and non-limited, fatty components, aqueous components, humectants, preservatives, texturizing agents, flavours, antioxidants and common pigments in the food sector.

The compositions comprising myo-inositol: D-chiroinositol in a weight ratio range between 1:1 to 9:1, respectively or the pharmaceutical compositions can occur at any pharmaceutical form of administration considered appropriate for the selected administration route, for example, by systemic (e.g intravenous, subcutaneous, intramuscular injection), oral, parenteral or topical administration, for which it will include the pharmaceutically acceptable excipients necessary for formulation of the desired method of administration. A preferred route of delivery is oral. In another preferred embodiment, the route of delivery is vaginal. Additionally, it is also possible to administer the composition of the invention as defined above, intranasally or sublingually which allows systemic administration by a non-aggressive mode of administration. In addition, it is possible to administer the composition via vaginal administration. Preferred administration forms are vaginal suppositories, vaginal tablets, vaginal ovula, vaginal rings or semi-solid vaginal preparations such as ointments, creams or gels.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a composition of the present invention including encapsulation in liposomes, microparticles, microcapsules and the like.

Where necessary, the composition is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

Solid dosage forms for oral administration may include conventional capsules, sustained release capsules, conventional tablets, sustained-release tablets, modified-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings. In addition, dosage forms for oral administration of the nutritional composition or nutraceutical used in the method of the invention may be in the form of nutritional beverages, puddings, confections (i.e., candy), ice cream, frozen confections, or non-baked extruded food. The nutritional supplement can be formulated into a snack to be taken as part of a diet.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration, the composition of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, the composition of the invention as defined above, or a pharmaceutically acceptable composition to be used according to the present invention may be administered in the form of transdermal patches or iontophoresis and electroporation devices. In one embodiment, the composition of the invention is administered as a transdermal patch, for example, in the form of sustained-release transdermal patch. Suitable transdermal patches are known in the art.

Several drug delivery systems are known and can be used to administer the composition of the invention, including, for example, encapsulation in liposomes, microbubbles, emulsions, microparticles, microcapsules and similars. The required dosage can be administered as a single unit or in a sustained release form.

Sustainable-release forms and appropriate materials and methods for their preparation are described in, for example, "Modified-Release Drug Delivery Technology", Rathbone, M. J. Hadgraft, J. and Roberts, M. S. (eds.), Marcel Dekker, Inc., New York (2002), "Handbook of Pharmaceutical Controlled Release Technology", Wise, D. L. (ed.), Marcel Dekker, Inc. New York, (2000). In one embodiment of the invention, the orally administrable form of a composition to be used according to the invention is in a sustained release form further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of the them. Enteric coatings may be applied using conventional processes known to experts in the art, as described in, for example, Johnson, J. L., "Pharmaceutical tablet coating", Coatings Technology Handbook (Second Edition), Satas, D. and Tracton, A. A. (eds), Marcel Dekker, Inc. New York, (2001), Carstensen, T., "Coating Tablets in Advanced Pharmaceutical Solids", Swarbrick, J. (ed.), Marcel Dekker, Inc. New York (2001), 455-468.

In a preferred embodiment the composition used in the method of the invention is in a solid dosage forms for oral administration.

In a more preferred embodiment, the composition to be used in the method of the invention may be in the form of powders, granules, granulates, sachets, tablets, capsules, effervescence tablets, chewable tablets, pills, cachets, immediate release tablets and modified release tablets, as well as fluid or liquid formulations, such as, for example, solutions, suspensions, emulsions, dispersions and mixtures. Moreover, the composition can be in the form of powders, dispersible powders or granules suitable for preparing an aqueous suspension by adding a liquid medium, such as, for example, an aqueous medium. In an even more preferred embodiment, the composition to be used in the method of the invention is in the form of a capsule, more particularly is in a soft capsule.

The term "soft capsule" is well known in the art and refers to are a single-unit solid dosage form, consisting of a liquid or semi-solid fill enveloped by a one-piece hermetically sealed elastic outer shell. The capsule has a soft capsule shell, as opposed to hard capsules that are made up of a rigid shell. Depending on the polymer forming the shell, they can be subdivided into two categories, namely soft gelatin capsules or 'softgels' and non-gelatin soft capsules.

A soft capsule shell is generally made of gelatin, water and plasticizer in various mixtures which gives elasticity and softness to the walls (shell). Soft capsules are usually formed in a single piece, as opposed to hard capsules that are made up of a shell in two pieces that fit together.

In a preferred embodiment, the soft capsule comprises a gelatin shell.

In one embodiment, the soft capsule shell comprises gelatin and a plasticizer selected from the group consisting of glycerol, sorbitol, propylene glycol, polyethylene glycol, dibutyl sebacate, diethyl phthalate, dimethyl phthalate, triacetin, tributyl citrate, triethyl citrate, and mixtures thereof; preferably a plasticizer selected form the group consisting of glycerol, sorbitol, and mixtures thereof.

The gelatins used for making soft capsules shells those approved by local authorities for pharmaceutical or nutritional use. These gelatins are mainly of two different types either alkaline (Type B) or acid (Type A) with medium gel strength (medium Bloom, such as 150-200 Bloom). Both types may be used in combination or separately. Preferably, a combination of gelatin type A and gelatin type B is used. Examples of type B gelatins are limed bone gelatins and limed hide gelatin. Examples of type A gelatins are pig skin gelatin, acid hide gelatin and fish gelatin.

In one embodiment, the soft capsule shell further comprises a pharmaceutically acceptable opacifying agent and/or a pharmaceutically acceptable coloring agent. Opacifying agents are added to the soft capsule shell in order to make the shell opaque and thus protect the soft capsule filling, i.e. the pharmaceutical composition, from light. Suitable opacifying agents are known in the art and include titanium dioxide, talc, and the like. Coloring agents are added to the soft capsule shell to give the shell the desired color. Suitable coloring agents are known in the art and include sunset yellow FCF (E-110), indigo carmine (E-132), erythrosine (E-127), quinoline yellow (E-104), iron oxides E-172 yellow or brown, titanium dioxide E-171, and the like.

In further embodiment, the composition to be used according to the invention further comprises calcium or a pharmaceutically acceptable derivative thereof, preferably calcium ions (Ca2+). Calcium and pharmaceutically acceptable derivatives thereof refers to any pharmaceutically acceptable source of calcium or calcium ions, such as pharmaceutically acceptable calcium salts, calcium hydroxide and hydroxyapatite. Examples of said pharmaceutically acceptable calcium salts are calcium carbonate, chloride, chloride hexahydrate, citrate, formate, glycinate, bisglycinate, glucoheptonate, gluconate, gluconolactate, glutamate, glycerophosphate, hydrogenophosphate, lactate, lactobionate, lactophosphate, levulinate, oleate, monobasic or tribasic phosphate, pidolate, sulfate. Preferably, the calcium or calcium ion is provided as calcium glycinate, calcium bisglycinate, calcium hydroxide or mixtures thereof. More preferably, the calcium or calcium ion is provided as calcium glycinate, calcium bisglycinate, or mixtures thereof.

In a further embodiment, the composition of the invention further comprises iron or a pharmaceutically acceptable derivative thereof; vitamin B12; vitamin B9 (also known as folic acid or folate); vitamin D, levomefolic acid or a pharmaceutically acceptable salt thereof; and/or essential unsaturated fatty acids or mixtures thereof.

Iron and derivatives thereof refers to any pharmaceutically acceptable source of iron, such as iron ions (Fe2+ and/or Fe3+), which may be provided as pharmaceutically acceptable iron salts; and elemental iron, which may be provided as a metalloprotein or as a coordination complex, wherein the iron (Fe(III) or Fe(II)) is coordinated by nitrogen, oxygen or sulfur centres belonging to amino acid residues of a protein or another pharmaceutically acceptable organic compound. Examples of said pharmaceutically acceptable iron salts are ferrous salts and ferric salts, preferably such as ferric ammonium citrate, ferric phosphate, ferric pyrophosphate, ferritin, ferrocholinate, ferrous ascorbate, ferrous aspartate, ferrous chloride, ferrous sulfate, ferrous tartrate, ferrous fumarate, ferrous gluconate, ferrous gluceptate, ferrous glycine sulfate, ferrous lactate, ferrous oxalate and ferrous succinate. Examples of said iron metalloproteins or coordination complexes are iron glycinate complex, iron glucose complex, iron fructose complex, iron polymaltose complex, and iron sucrose complex.

For use in the present invention, the composition is present is administered in an effective amount.

The term "effective" amount or a "therapeutically effective amount" of a drug or pharmacologically active agent is meant a nontoxic but sufficient amount of the drug or agent to provide the desired effect.

Even though individual needs vary, determination of optimal ranges for effective amounts of the composition of the invention belongs to the common experience of those experts in the art. In general, the dosage needed to provide an effective amount of such compound, which can be adjusted by one expert in the art will vary depending on age, health, fitness, sex, diet, weight, frequency of treatment and the nature and extent of impairment or illness, medical condition of the patient, route of administration, pharmacological considerations such as activity, efficacy, pharmacokinetic and toxicology profile of the particular composition used, if using a system drug delivery, and if the compound is administered as part of a combination of drugs.

The effective quantity of the composition of the invention can vary within a wide range and, in general, will vary depending on the particular circumstances of application, duration of the exposure and other considerations.

In a preferred embodiment, if the composition contains 550 mg of myo-inositol and 150 mg of D-chiro-lnositol and the female subject is a human then it is administered twice a day, and wherein if the composition contains 1100 mg of myo-inositol and 300 mg of D-chiro-lnositol and the female subject is a human, then the composition is administered once a day.

In a preferred embodiment of the methods of the invention, the composition is administered at least 12 weeks.

Medical Uses

In another aspect, the invention relates to a composition comprising myo-inositol and D-chiro-lnositol in a weight ratio between 1:1 to 9:1, respectively, for use in the treatment or prevention of polycystic ovary syndrome in a female subject, (first medical use).

Alternatively, the invention relates to a method for treating or preventing polycystic ovary syndrome comprising administering a composition comprising myo-inositol and D-chiro-lnositol in a weight ratio between 1:1 to 9:1, respectively, to a female subject in need of treatment.

Alternatively, the invention relates to a composition comprising myo-inositol and D-chiro-lnositol in a weight ratio between 1:1 to 9:1, respectively, for the preparation of a medicament for the treatment or prevention of polycystic ovary syndrome in a female subject.

In another aspect, the invention relates to a composition comprising myo-inositol and D-chiro-lnositol in a weight ratio between 1:1 to 9:1, respectively, for use in the treatment or prevention of infertility in a female subject suffering polycystic ovary syndrome (second medical use).

Alternatively, the invention relates to a method for treating or preventing infertility of a female subject suffering polycystic ovary syndrome comprising administering a composition comprising myo-inositol and D-chiro-lnositol in a weight ratio between 1:1 to 9:1, respectively, to a female subject in need of treatment.

Alternatively, the invention relates to a composition comprising myo-inositol and D-chiro-lnositol in a weight ratio between 1:1 to 9:1, respectively, for the preparation of a medicament for the treatment or prevention of infertility in a female subject suffering polycystic ovary syndrome.

"Infertility" as used herein, relates to the inability of a woman to reproduce by natural means. Particularly, is a disease of the reproductive system defined by the failure to achieve a clinical pregnancy after 12 months or more of regular unprotected sexual intercourse (and there is no other reason, such as breastfeeding or postpartum amenorrhoea). The infertility can be produce by several reasons. In a preferred embodiment, the female subject to be treated shows failure in embryo implantation.

In another aspect, the invention relates to a composition comprising myo-inositol and D-chiro-lnositol in a weight ratio between 1:1 to 9:1, respectively, for use in preventing or reducing the risk of ovarian hyperstimulation syndrome in a female subject suffering polycystic ovary syndrome and subjected to ovary stimulation treatment (third medical use).

Alternatively, the invention relates to the use of a composition comprising myo-inositol and D-chiro-lnositol in a weight ratio between 1:1 to 9:1, respectively in the preparation of a medicament for preventing or reducing the risk of ovarian hyperstimulation syndrome in a female subject suffering polycystic ovary syndrome and subjected to ovary stimulation treatment.

Alternatively, the invention relates to a method for preventing or reducing the risk of ovarian hyperstimulation syndrome in a female subject suffering polycystic ovary syndrome and subjected to ovary stimulation treatment, the method comprising administering a composition comprising myo-inositol and D-chiro-lnositol in a weight ratio between 1:1 to 9:1, respectively to the subject in need thereof.

"Ovarian hyperstimulation syndrome" or OHSS as used herein, relates to a medical condition that can occur in some women who take fertility medication to stimulate egg growth. OHSS has been characterized by the presence of multiple luteinized cysts within the ovaries leading to ovarian enlargement and secondary complications. The central feature of clinically significant OHSS is the development of vascular hyperpermeability and the resulting shift of fluids into the third space. Ovarian hyperstimulation syndrome is particularly associated with injection of a hormone called human chorionic gonadotropin (hCG) which is used for inducing final oocyte maturation and/or triggering oocyte release. The risk is further increased by multiple doses of hCG after ovulation and if the procedure results in pregnancy.

In a preferred embodiment, the female subject is subjected to an ovary stimulation treatment, more preferably before the medical uses of the invention. In a more preferred embodiment, the ovary stimulation treatment is gonadotropin-releasing hormone antagonist and/or FSH.

As used herein the terms "treat," "treatment," or "treatment of" refers to reducing the potential for a certain disease or disorder, reducing the occurrence of a certain disease or disorder, and/or a reduction in the severity of a certain disease or disorder, preferably, to an extent that the subject no longer suffers discomfort and/or altered function due to it. For example, "treating" can refer to the ability of a composition of the invention when administered to a subject, to prevent a certain disease or disorder from occurring and/or to cure or to alleviate a certain disease symptoms, signs, or causes. "Treating" also refers to mitigating or decreasing at least one clinical symptom and/or inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes. Particularly, "treatment", as used herein, relates to the administration of a composition according to the invention or of a pharmaceutical composition according to the invention to a female subject suffering from polycystic ovary syndrome including the administration in an initial or early stage of a disease, wherein the object is to prevent or slow down (lessen) an undesired physiological change or disorder.

The present disclosure provides methods and compositions generally providing a therapeutic benefit or desired clinical results. A therapeutic benefit is not necessarily a cure for a particular disease or disorder, but rather encompasses a result which most typically includes alleviation of the disease or disorder or increased survival, elimination of the disease or disorder, reduction or alleviation of a symptom associated with the disease or disorder, prevention or alleviation of a secondary disease, disorder or condition resulting from the occurrence of a primary disease or disorder, diminishment of extent of disease, stabilized (i.e., not worsening) state of disease, delay or slowing of disease progression, amelioration or palliation of the disease state, and remission (whether partial or total), whether detectable or undetectable and/or prevention of the disease or disorder. Treatment also means prolonging survival as compared to expected survival if not receiving the treatment. In a preferred embodiment, the term treatment relates to alleviation of at least one symptom of the disease selected form the group consisting of, infertility, insulin resistance, hirsutism, alopecia, acne, overweight. In another preferred embodiment, the term encompasses the alleviation of two or more symptoms of PCOS.

The term "prevention", "preventing" or "prevent", as used herein, relates to the administration of a composition according to the invention or of a pharmaceutical composition according to the invention to a female subject who has not been diagnosed as possibly having polycystic ovary syndrome, or ovarian hyperstimulation syndrome at the time of administration, but who would normally be expected to develop said disease or be at increased risk for said disease. The prevention intends to avoid the appearance of said disease. The prevention can be complete (e.g. the total absence of a disease). The prevention can also be partial, such that for example the occurrence of a disease in a subject is less than that which would have occurred without the administration of the combination or composition of the present invention. Prevention also refers to reduced susceptibility to a clinical condition. The prevention also includes reducing the risk of suffering the disease. The terms "composition", "myo-inositol", "D-chiroinositol" and its embodiments have been previously described and are equally applicable to this aspect of the invention.

In a preferred embodiment of the medical uses of the invention, the composition comprises myo-inositol: D-chiroinositol in a weight ratio range between 1:1 to 3:1, more preferably 1:1, 1.5:1, 2:1, 2.5:1 or 3:1. In another referred embodiment, the myo-inositol: D-chiroinositol is in a weight ratio range between 3:1 to 5:1, more preferably 3:1, 3.5:1, 4:1, 4.5:1 or 5:1. In another referred embodiment, the myo-inositol: D-chiroinositol is in a weight ratio range between 5:1 to 7:1, more preferably 5:1, 5.5:1, 6:1, 6.5:1 or 7:1. In another referred embodiment, the myo-inositol: D-chiroinositol is in a weight ratio range between 7:1 and 9:1, more preferably 7:1, 7.5:1, 8:1, 8.5:1 or 9:1.

In another referred embodiment, the myo-inositol: D-chiroinositol is in a weight ratio range between 2:1 to 5:1, more preferably between 2:1, 2.5:1, 3:1, 3.5:1, 4:1, 4.5:1 and 5:1. In another preferred embodiment, the weight ratio of myo-inositol:D-chiroinositol is 3.1:1, 3.2:1, 3.3:1, 3.4:1, 3.5:1, 3.6:1, 3.7:1, 3.8:1 or 3.9:1. In a more preferred embodiment, the weight ratio of myo-inositol:D-chiroinositol is 3.66:1.

As the person skilled in the art can understand the desirable weight ratio of myo-inositol:D-chiroinositol can be obtained with different amounts of myo-inositol and D-chiroinositol, all of them encompasses in the present invention. In a preferred embodiment of the medical uses of the invention the contents of myo-inositol and D-chiro-Inositol in the composition are 550 mg of myo-inositol and 150 mg of D-chiro-Inositol or 1100 mg of myo-inositol and 300 mg of D-chiro-lnositol.

In another preferred embodiment, the composition to be administered according to the medical uses of the invention comprises between 1000 mg and 2000 mg of myo-inositol. In another preferred embodiment, the contents of myo-inositol and D-chiro-Inositol in the composition are 1000 mg of myo-inositol and 150 mg of D-chiro-lnositol. In another preferred embodiment, the contents of myo-inositol and D-chiro-lnositol in the composition are 2000 mg of myo-inositol and 300 mg of D-chiro-lnositol.

In another preferred embodiment wherein if the composition contains 550 mg of myo-inositol and 150 mg of D-chiro-lnositol and the female subject is a human then it is administered twice a day, and wherein if the composition contains 1100 mg of myo-inositol and 300 mg of D-chiro-lnositol and the female subject is a human, then the composition is administered once a day. In a preferred embodiment the composition is administered at least 12 weeks.

In a preferred embodiment the composition used in the method of the invention is in a solid dosage forms for oral administration.

In a more preferred embodiment, the composition to be used in the method of the invention may be in the form of powders, granules, granulates, sachets, tablets, capsules, effervescence tablets, chewable tablets, pills, cachets, immediate release tablets and modified release tablets, as well as fluid or liquid formulations, such as, for example, solutions, suspensions, emulsions, dispersions and mixtures. Moreover, the composition can be in the form of powders, dispersible powders or granules suitable for preparing an aqueous suspension by adding a liquid medium, such as, for example, an aqueous medium. In an even more preferred embodiment, the composition to be used in the method of the invention is in the form of a capsule, more particularly is in a soft capsule. In a preferred embodiment, the soft capsule comprises a gelatin shell.

In a preferred embodiment of the medical uses of the invention, the composition further comprises a compound suitable for treating polycystic ovary syndrome.

Most prescribed treatments address specific manifestations of PCOS and do not address underlying causes of the disease. Compounds suitable for treating polycystic ovary syndrome, or any of its manifestations are for example, androgen excess and associated symptoms (e.g., hirsutism, acne) are commonly treated with estrogen-progestin contraceptives, antiandrogens, anti-acne treatments, and prescription drugs and over-the-counter depilatories for removing or slowing unwanted hair growth, such as spironolactone, fluramine, finasteride or eflornithine. Additionally, anovulation and fertility issues are treated with ovulation promoting drugs (e.g., clomiphene, letrozole, or follicle stimulating hormone (FSH) injections). Other treatments are prescribed for PCOS patients having hypertension (e.g., anti-hypertensive medications), hyperlipidemia (e.g., statins, other cholesterol lowering agents), and insulin-resistance/Type 2 diabetes (e.g., metformin, other diabetic medications).

All the terms and embodiments previously described are equally applicable to this aspect of the invention.

Soft Capsule and Process for Preparing

In another aspect, the invention relates to a soft capsule comprising:
a) a soft capsule shell and
b) a pharmaceutical composition comprising myo-inositol and D-chiro-lnositol in a weight ratio between 1:1 to 9:1 respectively.

The terms "soft capsule", "pharmaceutical composition", "myo-inositol", "D-chiro-Inositol" and its embodiments have been previously described in relation to the method for increasing embryo implantation and are equally applicable to this aspect of the invention. In a preferred embodiment, the shell further comprises gelatin.

In a preferred embodiment, the composition comprises myo-inositol: D-chiroinositol in a weight ratio range between 1:1 to 3:1, more preferably 1:1, 1.5:1, 2:1, 2.5:1 or 3:1. In another referred embodiment, the myo-inositol: D-chiroinositol is in a weight ratio range between 3:1 to 5:1, more preferably 3:1, 3.5:1, 4:1, 4.5:1 or 5:1. In another referred embodiment, the myo-inositol: D-chiroinositol is in a weight ratio range between 5:1 to 7:1, more preferably 5:1, 5.5:1, 6:1, 6.5:1 or 7:1. In another referred embodiment, the myo-inositol: D-chiroinositol is in a weight ratio range between 7:1 and 9:1, more preferably 7:1, 7.5:1, 8:1, 8.5:1 or 9:1.

In another referred embodiment, the myo-inositol: D-chiroinositol is in a weight ratio range between 2:1 to 5:1, more preferably between 2:1, 2.5:1, 3:1, 3.5:1, 4:1, 4.5:1 and 5:1. In another preferred embodiment, the weight ratio of myo-inositol:D-chiroinositol is 3.1:1, 3.2:1, 3.3:1, 3.4:1, 3.5:1, 3.6:1, 3.7:1, 3.8:1 or 3.9:1. In a more preferred embodiment, the weight ratio of myo-inositol:D-chiroinositol is 3.66:1.

As the person skilled in the art can understand the desirable weight ratio of myo-inositol:D-chiroinositol can be obtained with different amounts of myo-inositol and D-chiroinositol, all of them encompasses in the present invention. In a preferred embodiment the contents of myo-inositol and D-chiro-lnositol in the composition are 550 mg of myo-inositol and 150 mg of D-chiro-lnositol or 1100 mg of myo-inositol and 300 mg of D-chiro-lnositol.

In another preferred embodiment, the composition comprises between 1000 mg and 2000 mg of myo-inositol. In another preferred embodiment, the composition comprises between 300 mg and 500 mg of D-chiro-lnositol. In another preferred embodiment, the contents of myo-inositol and D-chiro-lnositol in the composition are 1000 mg of myo-inositol and 150 mg of D-chiro-lnositol. In another preferred embodiment, the contents of myo-inositol and D-chiro-lnositol in the composition are 2000 mg of myo-inositol and 300 mg of D-chiro-lnositol.

In another aspect, the invention relates to a process for preparing a soft capsule according to the invention.

The soft capsules of the present invention can be prepared by any conventional manufacturing process known in the art for the preparation of soft capsules (as described for example in Gurava reddy, R. et al., Int. J. Adv. Pharm. Gen. Res., 2013, 1, 20-29), such as plate process, by a rotary-die process, reciprocating die or accogel machine. As a way of illustrative non limitative example of preparation of gelatin capsules the plate process comprises placing the gelatin sheet over a die plate containing numerous die pockets, applying vacuum to draw the sheet in to the die pockets, filling the pockets with liquid or paste, place another gelatin sheet over the filled pockets, and sandwich under a die press where the capsules are formed and cut out. As a way of illustrative non limitative example, in the rotary die process, the pharmaceutical composition to be encapsulated flows by gravity and the gelatin sheets are feed on rolls contain small orifice lined up with the die pocket of the die roll. Two plasticized gelatin ribbons are continuously and simultaneously fed with the liquid or paste fill between the rollers of the rotary die mechanism where the capsule are simultaneously filled, shaped, hermetically sealed and cut from the gelatin ribbon. The sealing of the capsule may be achieved by mechanical pressure on the die rolls and the heating(37-40C) of the ribbons by the wedge. All the terms and embodiments previously described are equally applicable to this aspect of the invention.

The following examples illustrate the invention and should not be considered as limitative of the invention.

EXAMPLES

Materials and Methods
Study Design

This study was a double blind, two-arm, Phase 2/Phase 3; multicentre randomized clinical trial (RCT) with quadruple masking (Participant, Care Provider, Investigator and Outcomes Assessor). This study was conducted at five sites in Spain from February 2016 to April 2017 and was performed in accordance with the Declaration of Helsinki and Good Clinical Practice guidelines; it is registered at clinicaltrials.gov with the identifier NCT03201601.

For a superiority trial to test that the pregnancy rate is higher under experimental treatment, with double the pregnancy rate than under normal treatment, assuming a 30% pregnancy rate under control treatment with a statistical power of 80% and a significance level of 5%, the sample per group needed was 30 patients per group. That is for testing a pregnancy rate of 60% in the treatment group (a margin of 30%), and therefore the sample need is 30 patients per group.

Subjects

Women with PCOS who were planning to receive an intracytoplasmic sperm injection (ICSI) were screened for possible study inclusion and enrolled prior to oocyte retrieval and embryo transfer (the recruitment period was February 2016 to April 2017; the last subject was randomized on 19 Apr. 2017). Patients were screened for eligibility and provided informed consent for the intended clinical trial after their diagnosis of PCOS was confirmed.

Inclusion criteria: The study enrolled women between 18-40 years old with PCOS according to the Rotterdam criteria with BMI <30 and baseline FSH <10 IU/l who were undergoing ICSI and freely agreed to participate in the study and sign the informed consent document. All participants were required to have a normal uterine cavity.

Exclusion Criteria:

Contraindications for ICSI, congenital adrenal hyperplasia, hyperprolactinemia, thyroid disease, severe endometriosis (III or IV stage), poor responder in previous fertility treatments, low compliance and/or collaboration expectations, and severe male factor (Cryptozoospermic).

Methods

The trial was designed to test whether MYO/DCI (3,6:1) was a superior treatment to MYO/DCI (40:1) for the ICSI parameters and to achieve pregnancy in women with PCOS undergoing ICSI.

Sixty subjects were randomized to receive either oral 550 mg of MYO+150 mg of DCI twice daily (3.6:1) (Study group-SG-) or 550 mg of MYO+13.8 mg of DCI twice daily (40:1) (Control group-CG-) over 12 weeks. DCI and MYO were provided by Biosearch Life (Spain). DCI was obtained from *Ceratonia* siliqua L. (Caronositol®), The two treatments were administered in soft gelatin capsules that had the same appearance without any reference to their contents, so that neither the volunteers nor researchers of the study would know the group to which they belonged. Each participant consumed two capsules of each treatment daily, in the morning and at night, without any restriction in their diet nor their daily habits. Intake of other vitamins or antioxidants was not permitted during the study with the exception of folic acid (400 ug/day). Patients continued to take the study medication until a pregnancy test (two weeks after embryo transfer).

Initial ovulation stimulation was performed homogeneously in all participating centres using a GnRH antagonist cycle and an initial dose of 150 units of recombinant FSH for five days (Gonal-F, Merck Serono, Switzerland; Puregon, MSD; USA). After the initial stimulation, each patient was treated individually according to her response, which was measured every two days by vaginal ultrasound, as well as according to the estradiol and LH levels. Triggering was performed with 0.2 mg of triptorelin (Decapeptyl; Ferring, Switzerland) in all cases. Follicular puncture was scheduled approximately 36-37 hours after triggering. Embryo transfer was carried out individually according to the characteristics of each volunteer and her response, although in no case was more than three embryos transferred. In all cases in which an embryo transfer was made, treatment with micronized natural progesterone (Progeffik, Effik; Utrogestan, SEID (at a dose of 400 mg daily) for luteal phase support was prescribed.

Measurements

At screening, visits were standardized across all study sites, and each site used identical case report forms prepared by the Data Coordination Center at Biosearch. The forms and procedures for data collection were identical for both cohorts.

BMI was calculated from height and weight measurements performed during the screening visit. Participants were weighed while dressed in light clothing, without shoes. Height was measured without shoes. Hirsutism was assessed in all participants using the Ferriman-Gallwey hirsutism scoring scale (Ferriman and Gallwey, 1961).

Two blood samples of 7.5 ml each were taken at the beginning and end of treatment. The extraction and samples were analysed in the corresponding clinic. The inventors used HOMA (homeostatic model assessment for assessing insulin sensitivity) as a measure of insulin resistance (IR) (Majid et al 2017). Insulin levels were determined by a chemiluminescence immunoassay, and the total plasma testosterone concentrations were determined using Enzyme Linked Fluorescent Assay (ELFA).

Outcomes

The primary outcome was the pregnancy rate, and the secondary outcomes were oocyte quality, embryo quality, testosterone levels and insulin sensitivity.

Oocyte quality was defined by the percentage of metaphase II (MII) oocytes. Embryo quality was defined according the number of blastomeres, degree of fragmentation, multinucleation, and size of the blastomeres:

Very good quality (A): 4/8 mononuclear blastomeres of equal size on day +2/3 with <10% of fragmentation Good quality (B): >50% of the blastomeres with a number and size appropriate to the stage of development; mononuclear cells with 10-25% of fragmentation Poor quality (C): >50% of the blastomeres with a number and size that are not appropriate to the stage of development; multinucleation with >25% of fragmentation Participants who conceived were followed at the clinical site for ultrasound evidence of a viable intrauterine pregnancy (foetal heart motion) and referred for obstetrical care. Information on the pregnancy progress and delivery outcomes was obtained by an infant and maternal medical record review. The pregnancy outcomes were defined as:

Pregnancy was defined as a positive test at two weeks from embryo transfer.

Clinical Pregnancy: pregnancy with sonographic visualization of one or more gestational sacs.

Ongoing pregnancy: pregnancy with ultrasonographic visualization of one or more gestational sacs and a foetal heartbeat after 12 weeks of gestation Clinical pregnancy rate per cycle: percentage of patients who became pregnant per cycle of stimulation performed.

Clinical pregnancy rate by transfer: percentage of patients who became pregnant due to embryo transfer.

Implantation rate: percentage of embryos that was implanted in the uterus after the transfer.

Ethical Approval

The study was approved at each clinical site. Each patient was assigned a key to ensure the confidentiality of their analytical values. Patients signed an informed consent document informing them about the procedure and the possible risks of the study. ICSI was performed in all cases in the circumstances of normal sperm, the patients were informed of possible higher foetal anomalies in ICSI vs IVF.

Dropout

Study dropouts refer to participants who withdrew from the treatment and trial and were lost to follow-up in the study. Women who dropped out were excluded from the final analyses.

There were no significant differences between treatment groups with regard to the reason for withdrawal. Similar proportions and reasons for dropout were observed in the two treatment groups: one woman in the SG for personal reasons (3.45%); two women in the CG, one for personal reasons and one by accident (7.41%). Most of personal reasons were that these individuals decided not to undergo ICSI.

Statistical Methodology

First, a description of the sample and personal information of the women, including their tobacco use, alcohol consumption, activity and clinical history, was provided by the treatment group. Bivariate statistical tests for the personal variables given in the treatment undertaken were performed to determine the homogeneity of the women's characteristics between treatment groups. Frequencies and percentages were calculated, and chi-square tests (exact or asymptotic, depending on the frequency distribution) were performed on qualitative variables. For quantitative variables, the mean, standard deviation (SD) and 95% confidence intervals were obtained and the asymptotic t-test or bootstrap technique for the t-test (depending on normality assumption) were performed to compare groups. In addition, similar analyses were carried out for the subset of women who completed the study to gather information about the oocytes and embryos.

Then, description analyses of the primary and secondary outcomes were performed. The number of oocytes was summarized by the mean and SD per group, as well as considering the counting data within the group, providing the incidence rates of oocytes for each group and incidence rate ratio (IRR) with the 95% confidence interval. The same approach was used to summarize the number of embryos. The number of mature oocytes was described by the mean and SD per group. In addition, the response considering a binomial distribution, with n as the total number of oocytes and p as the probability of being a mature oocyte from the n possible oocytes from a patient, was summarized as the odds of success of mature oocytes per group and OR (95% confidence interval). Similar data calculations were obtained for the number of embryos of type A, B or C from all embryos from a patient. Furthermore, the ratio of mature oocytes in each patient was calculated, and differences in the ratios between groups were checked and tested. The main outcome success of pregnancy was described as the frequency and percentage per group as well as with the odds of pregnancy per group, with the corresponding OR and its confidence interval. The number of days of stimulation was categorized as smaller or equal to 10 days and higher than 10 days, and the frequencies and percentage were determined per group, and \a chi-squared test was performed. With regards to transferred embryos, responses were classified as lower or equal to 1, 2 or >2 transfer embryos. Testing of differences in the distributions of responses per group was performed with a chi-square t-test. The number of bags was also compared between groups using a chi-square test, and the odds of one or more bags were calculated.

To conclude the effect of treatment with the probability of success of mature oocytes and pregnancy, multivariate generalized regression models were applied.

The models were fitted by individual patient characteristics, and the adjusted odds ratios for the treatment groups were obtained.

Glucose, insulin. HOMA and testosterone were compared between groups at baseline and at the end of the study. An independent-test was used at each time point to test the differences of the mean values between groups. In addition, statistical multivariate modelling was applied to check differences between groups with regard to the evolution of parameters, which used multivariate linear mixed regression models with and intra-subject random effect and was fitted with the patients' characteristics.

For the selection procedure of the multivariate model, manual introduction in a step forward method was used, where the variables were investigated as possible confounders and the interaction terms between the variables introduced in the model was carried out. When variable selection using the method described was finished, a second procedure using the manually backward stepwise method was performed to check for possible changes in the effects of variables that were initially discarded. Significant effects of the individual factors, changes in the estimated parameters if the variable was discarded, the Bayesian Information criterion and the AIK information criterion were checked across all steps of model selection. The R project 3.3. was used.

Example 1

Sixty women with PCOS were randomized for inclusion in this study. Four women were excluded after randomization and consent were completed due to personal reasons (they decided not to undergo ICSI or because they met the exclusion criteria. Finally, 56 (93.33%) women with PCOS participated in the study.

At baseline, no differences were found between the two groups (see Table 1).

TABLE 1

Patients' characteristics at baseline

| | Study Group (N = 29) | | Control Group (N = 27) | | |
|---|---|---|---|---|---|
| | Mean (SD) | 95% CI (LL, UL) | Mean (SD) | 95% CI (LL, UL) | T-test p-value |
| Quantitative patients' characteristics at baseline | | | | | |
| Age | 31.67 (0.86) | (29.91-33.42) | 31.74 (0.89) | (29.91-33.57) | 0.953 |
| Weight | 67.31 (2.33) | (62.53-72.09) | 67.11 (2.09) | (62.82-71.4) | 0.950 |
| Height | 162.67 (1.32) | (159.97-165.37) | 164.11 (1.06) | (161.93-166.29) | 0.404 |
| BMI | 25.51 (0.86) | (23.73-27.28) | 24.88 (0.69) | (23.45-26.3) | 0.576 |
| Time of sterility | 3.35 (0.36) | (2.69-4) | 2.57 (0.24) | (2.13-3.04) | 0.088* |
| Qualitative patients' characteristics at baseline N (%) | | | | | |
| Regular activity | 10 (33.33%) | | 6 (22.22%) | | 0.351 |
| Alcohol consumption | 9 (30%) | | 6 (22.22%) | | 0.506 |
| Smoking | 7 (23.33%) | | 7 (25.93%) | | 0.820 |
| No previous pregnancy | 28 (93.33%) | | 23 (85.19%) | | 0.408 |

*Bootstrap estimates
BMI = body mass index

Three patients did not complete the study due to personal reasons (one in each group), and one woman in the CG did not complete the study due to an accident. Another nine subjects did not reach ovarian puncture: three left the study due to spontaneous pregnancy (two in the SG and one in the CG) and three were removed from the study due to the risk of ovarian hyperstimulation syndrome (OHSS) (one in the SG and two in the GC). Another three patients in the CG also did not undergo embryo transfer due to the risk of OHSS. Globally, the percentage of exclusions due to the risk of OHSS was lower in the SG (3.44 vs 18.5%, p=0.07). The follow-up of the participants is shown in FIG. 1.

When ET was not achieved due to the OHSS risk, insulin, glucose, and testosterone tests were performed at the time of ovarian puncture.

At the end of study, the duration of ovarian stimulation was similar in both groups. Likewise, the total testosterone, glucose and insulin levels, HOMA, number of MII oocytes and percentage of good-quality embryos were also similar in both groups (Table 2).

TABLE 2

Summary results for the qualitative secondary outcomes.

| | | Study Group | | | Control Group | | |
|---|---|---|---|---|---|---|---|
| | N | Mean (SD) | 95% CI (LL. UL) | N | Mean (SD) | 95% CI (LL. UL) | p-value |
| Number of Oocytes | 25 | 13.46 (1.01) | (11.38-15.54) | 22 | 13.76 (1.48) | (10.67-16.85) | 0.864 |
| No Mature oocytes | 25 | 3 (0.49) | (1.98-4.02) | 22 | 3.1 (0.55) | (1.98-4.25) | 0.898 |
| Mature oocytes | 25 | 10.46 (0.88) | (8.65-12.28) | 22 | 10.67 (1.57) | (7.4-13.94) | 0.910 |
| Ratio Mature oocytes/ N. oocytes | 25 | 0.77 (0.04) | (0.7-0.84) | 22 | 0.74 (0.05) | (0.63-0.84) | 0.575 |
| Number of Embryos | 25 | 6.88 (0.77) | (5.65-8.2) | 22 | 7.19 (1.41) | (4.52-9.89) | 0.858 |
| Embryos type A | 25 | 3.08 (0.71) | (2-4.27) | 22 | 3.86 (1.22) | (1.76-6.38) | 0.571 |
| Embryos type B | 25 | 1.5 (0.31) | (1-2.04) | 22 | 1.35 (0.44) | (0.75-2.1) | 0.467 |
| Embryos type C | 25 | 1.81 (0.38) | (1.15-2.49) | 22 | 1.6 (0.38) | (0.85-2.55) | 0.754 |
| Insulin at baseline | 29 | 11.75 (1.31) | (9.5-14.55) | 27 | 11.53 (2.12) | (8.28-15.38) | 0.929 |
| Insulin at end | 25 | 9.04 (0.95) | (7.22-11.16) | 22 | 9.05 (1.13) | (7.19-11.07) | 0.993 |
| Difference in insulin | 25 | 2.8 (1.04) | (1.15-4.83) | 22 | 2.97 (2.19) | (−0.64-7.41) | 0.951 |
| Testosterone at baseline | 29 | 0.57 (0.04) | (0.48-0.66) | 27 | 0.56 (0.05) | (0.45-0.67) | 0.911 |
| Testosterone at end | 25 | 0.41 (0.04) | (0.34-0.49) | 22 | 0.46 (0.05) | (0.36-0.56) | 0.430 |
| Difference of testosterone | 25 | 0.14 (0.03) | (0.07-0.21) | 22 | 0.12 (0.03) | (0.05-0.18) | 0.607 |
| Glucose at baseline | 29 | 90.82 (1.77) | (87.2-94.43) | 27 | 91.85 (2.48) | (87.81-96.88) | 0.757 |
| Glucose at the end | 25 | 85.96 (1.1) | (83.7-88.22) | 22 | 86.62 (1.51) | (83.49-89.76) | 0.720 |
| Difference in glucose | 25 | 4.61 (1.96) | (0.59-8.64) | 22 | 5.77 (2.55) | (1.58-11.28) | 0.727 |
| HOMA at baseline | 29 | 2.64 (1.66) | (2.02-3.26) | 27 | 2.65 (2.6) | (1.62-3.69) | 0.288 |
| HOM at the end | 25 | 1.94 (1.1) | (1.51-2.37) | 22 | 1.96 (1.23) | (1.43-2.49) | 0.719 |
| Difference in HOMA | 25 | 0.72 (1.31) | (0.21-1.24) | 22 | 0.82 (2.52) | (−0.27-1.91) | 0.408 |
| Day of stimulation | N | % | | N | % | | p-value |
| <=10 | 16 | 64 | | 15 | 68.18 | | 0.632 |
| >10 | 9 | 36 | | 7 | 31.82 | | |

Forty-five patients underwent embryo transfer (25 in the SG and 20 in the CG). No differences in the average number of embryos transferred nor the percentage of women with more than one embryo transferred were found. However, the pregnancy and live birth rates were significantly higher in the SG than in the CG (65.5 vs 25.9, p=0.003 and 55.2 vs 14.8, p=0.002). In addition, pregnancies after embryo transfer (ET) were higher in the SG than in the CG (68% vs 31.6%, p=0.017). The global data of each pregnancy rate is shown in Table 3.

TABLE 3

Pregnancy outcomes

| | | Number of cases per treatment group | | | 95% CI | | | 95% CI | | |
|---|---|---|---|---|---|---|---|---|---|---|
| | | SG | CG | Risk Ratio | Lower Limit | Upper Limit | OR(A/B) | Lower Limit | Upper Limit | p-value |
| Pregancy rate | No | 10 | 20 | 0.40 | 0.20 | 0.79 | 5.25 | 1.51 | 20.33 | 0.003 |
| | Yes | 19 | 7 | | | | | | | |
| Miscarriage rate | No | 16 | 4 | 2.71 | 0.71 | 10.42 | 0.27 | 0.02 | 2.76 | 0.146 |
| | Yes | 3 | 3 | | | | | | | |
| clinical pregnancy rate | No | 10 | 20 | 0.40 | 0.20 | 0.79 | 5.25 | 1.51 | 20.33 | 0.003 |
| | Yes | 19 | 7 | | | | | | | |
| Ongoing pregnancy rate | No | 13 | 23 | 0.27 | 0.10 | 0.70 | 6.81 | 1.72 | 34.12 | 0.002 |
| | Yes | 16 | 4 | | | | | | | |
| pregnancy rate by stimulation cycle | No | 8 | 16 | 0.40 | 0.19 | 0.84 | 5.44 | 1.38 | 24.35 | 0.005 |
| | Yes | 17 | 6 | | | | | | | |
| pregnancy by embryo transfer | No | 8 | 13 | 0.46 | 0.23 | 0.95 | 4.43 | 1.09 | 20.30 | 0.017 |
| | Yes | 17 | 6 | | | | | | | |

TABLE 3-continued

| | | Number of cases per treatment group | | | 95% CI | | | 95% CI | | |
|---|---|---|---|---|---|---|---|---|---|---|
| | | SG | CG | Risk Ratio | Lower Limit | Upper Limit | OR(A/B) | Lower Limit | Upper Limit | p-value |
| Live-Birth rate | No | 13 | 23 | 0.27 | 0.10 | 0.70 | 6.81 | 1.72 | 34.12 | 0.002 |
| | Yes | 17 | 4 | | | | | | | |

SG = Study Group;
CG = Control Group

A multivariate logistic regression model was applied for the success of pregnancy (variable Pregnancy Rate). There is a significant effect of treatment in the pregnancy results, being those women in the SG more likely to get pregnant than those in the CG. In particular the odds of pregnancy are 5.43 times higher in SG than in CG (OR=5.43; 95% CI (1.75, 18.61); p=0.022). None of the factors under the study were significantly associated with pregnancy. In addition, a logistic regression model was applied to estimate the probability of having >=1 bags (note that only one patient had 2 bags). A significant treatment effect was found, with lower probability of bags in the CG (OR=0.23; 95% CI (0.05, 0.85); p=0.043). None of the other factors considered were significantly associated with bags.

A post hoc calculation of the statistical power was performed to check the precision of the results under the reduced sample due to the dropouts of the study. The results show a 25.9% pregnancy rate under the control group and 65.5% under the experimental group, with 27 patients for CG and 29 patients for SG with a 5% significance level. The statistical power for the un-adjusted OR 0.19 is 0.852 for the control over the treatment and 0.980 for the adjusted OR=0.102.

With respect to testosterone levels, a linear mixed model with intra-subject random effect was fitted to the data. No significant differences between treatments were found at the end of the study adjusted to the baseline values (Difference of CG-SG=-0.007; 95% CI (-0.13, 0.12); p=0.904). A significant difference was found from baseline to end of the study, however the difference was similar in both groups (Dif=-0.13; 95% (-0.17, -0.08); p-value<0.001). The results from the multivariate model applied to the parameter HOMA show no significant effect of treatment p=0.875, although a decrease from baseline to end of study was observed in both groups (Dif=-0.70; 95% CI (-1.23, -0.16); p=0.011).

In conclusion, the combination of MYO-DCI at high doses of DCI improves the live-birth rate (and all other rates) with respect to its physiological concentration. This same combination reduces a risk of OHSS. These results highlight the importance of DCI supplementation in women with PCOS undergoing ICSI.

The invention claimed is:

1. A method for increasing embryo implantation rate in a uterus, said method comprising administering a composition comprising myo-inositol and D-chiro-inositol in a weight ratio of 3.66:1, respectively, to a female subject suffering polycystic ovary syndrome.

2. A method for preventing embryo implantation failure in a female subject suffering polycystic ovary syndrome, said method comprising administering a composition comprising myo-inositol and D-chiro-inositol in a weight ratio of 3.66:1, respectively, to said female.

3. A method for improving pregnancy rate, said method comprising administering a composition comprising myo-inositol and D-chiro-inositol in a weight ratio of 3.66:1, respectively, to a female subject suffering polycystic ovary syndrome.

4. A method for the treatment of polycystic ovary syndrome in a female subject, said method comprising administering a composition comprising myo-inositol and D-chiro-inositol in a weight ratio of 3.66:1, respectively, to said female subject.

5. A method for the treatment of infertility in a female subject suffering polycystic ovary syndrome, said method comprising administering a composition comprising myo-inositol and D-chiro-inositol, wherein the weight ratio of myo-inositol and D-chiro-inositol is 3.66:1 respectively, to said female subject.

6. A method for preventing or reducing the risk of ovarian hyperstimulation syndrome in a female subject suffering polycystic ovary syndrome and subjected to ovary stimulation treatment, said method comprising administering a composition comprising myo-inositol and D-chiro-inositol in a weight ratio of 3.66:1 respectively, to said female subject.

7. The method according to claim 6 wherein the ovary stimulation treatment is gonadotropin-releasing hormone antagonist and follicle stimulating hormone (FSH).

8. A soft capsule comprising:
a) a soft capsule shell; and
b) a pharmaceutical composition comprising myo-inositol and D-chiro-inositol in a weight ratio of 3.66:1, respectively.

9. The soft capsule according to claim 8, wherein the shell further comprises gelatin.

10. The method according to claim 1, wherein
the contents of myo-inositol and D-chiro-inositol are 550 mg of myo-inositol and 150 mg of D-chiro-inositol or 1100 mg of myo-inositol and 300 mg of D-chiro-inositol.

11. The method according to claim 2, wherein
the contents of myo-inositol and D-chiro-inositol are 550 mg of myo-inositol and 150 mg of D-chiro-inositol or 1100 mg of myo-inositol and 300 mg of D-chiro-inositol.

12. The method according to claim 3, wherein
the contents of myo-inositol and D-chiro-inositol are 550 mg of myo-inositol and 150 mg of D-chiro-inositol or 1100 mg of myo-inositol and 300 mg of D-chiro-inositol.

13. The method according to claim 4, wherein the contents of myo-inositol and D-chiro-inositol are 550 mg of myo-inositol and 150 mg of D-chiro-inositol or 1100 mg of myo-inositol and 300 mg of D-chiro-inositol.

14. The method according to claim 5, wherein the contents of myo-inositol and D-chiro-inositol are 550 mg of myo-inositol and 150 mg of D-chiro-inositol or 1100 mg of myo-inositol and 300 mg of D-chiro-inositol.

15. The method according to claim 6, wherein the contents of myo-inositol and D-chiro-inositol are 550 mg of myo-inositol and 150 mg of D-chiro-inositol or 1100 mg of myo-inositol and 300 mg of D-chiro-inositol.

16. The soft capsule according to claim 8, wherein the contents of myo-inositol and D-chiro-inositol in the pharmaceutical composition are of 550 mg of myo-inositol and 150 mg of D-chiro-inositol or of 1000 mg of myo-inositol and 300 mg of D-chiro-inositol.

* * * * *